(12) United States Patent
Baruth et al.

(10) Patent No.: US 10,136,872 B2
(45) Date of Patent: Nov. 27, 2018

(54) DETERMINATION OF AN X-RAY IMAGE DATA RECORD OF A MOVING TARGET LOCATION

(71) Applicants: Oliver Baruth, Erlangen (DE); Philipp Bernhardt, Forchheim (DE); Richard Obler, Erlangen (DE)

(72) Inventors: Oliver Baruth, Erlangen (DE); Philipp Bernhardt, Forchheim (DE); Richard Obler, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 87 days.

(21) Appl. No.: 15/078,007

(22) Filed: Mar. 23, 2016

(65) Prior Publication Data

US 2016/0278727 A1   Sep. 29, 2016

(30) Foreign Application Priority Data

Mar. 24, 2015  (DE) .................... 10 2015 205 270

(51) Int. Cl.
*G06K 9/00* (2006.01)
*A61B 6/00* (2006.01)
*G06T 5/00* (2006.01)
*G06T 5/50* (2006.01)

(52) U.S. Cl.
CPC .......... *A61B 6/5235* (2013.01); *A61B 6/5258* (2013.01); *G06T 5/003* (2013.01); *G06T 5/50* (2013.01); *A61B 6/4441* (2013.01); *G06T 2207/10016* (2013.01);

(Continued)

(58) Field of Classification Search
None
See application file for complete search history.

(56) References Cited

U.S. PATENT DOCUMENTS

| 7,181,082 B2* | 2/2007 | Feng ......................... G06T 5/10 250/201.2 |
| 8,938,112 B2* | 1/2015 | Park ....................... G06T 7/0012 378/4 |
| 9,129,426 B2* | 9/2015 | Gopalakrishnan .... G06T 11/005 |

(Continued)

FOREIGN PATENT DOCUMENTS

| EP | 2242021 A1 | 10/2010 |
| WO | WO2005093654 A2 | 10/2005 |

OTHER PUBLICATIONS

German Office Action for related German Application No. 10 2015 205 270.2, dated Dec. 9, 2015, with English Translation.

*Primary Examiner* — Soo Jin Park
(74) *Attorney, Agent, or Firm* — Lempia Summerfield Katz LLC

(57) ABSTRACT

A method and apparatus for determining an x-ray image data record of a target location subjected to a movement using an x-ray device. A number of basic images of the target location are recorded using a basic exposure time in each case and the x-ray image data record corresponding to an x-ray image with a longer exposure time is determined by combining basic images registered with one another. At least one quality value assigned hereto and relating to the movement in the target location during the recording is determined for each basic image and the contribution of a basic image to the x-ray image data record is determined as a function of the quality value.

11 Claims, 2 Drawing Sheets

(52) U.S. Cl.
CPC ............... *G06T 2207/10116* (2013.01); *G06T 2207/20216* (2013.01); *G06T 2207/30168* (2013.01)

(56) References Cited

U.S. PATENT DOCUMENTS

| | | | |
|---|---|---|---|
| 9,194,965 B2* | 11/2015 | Xu | G01T 1/295 |
| 9,314,161 B2* | 4/2016 | Wang | A61B 5/0044 |
| 2009/0169080 A1* | 7/2009 | Noordhoek | G06T 5/003 |
| | | | 382/131 |
| 2010/0165122 A1 | 7/2010 | Castorina et al. | |
| 2010/0220222 A1* | 9/2010 | Naito | H04N 5/217 |
| | | | 348/241 |
| 2011/0211758 A1 | 9/2011 | Joshi et al. | |
| 2012/0051664 A1* | 3/2012 | Gopalakrishnan | G06T 11/005 |
| | | | 382/294 |
| 2013/0182928 A1* | 7/2013 | Park | G06T 7/0012 |
| | | | 382/131 |
| 2013/0184570 A1* | 7/2013 | Wang | A61B 5/0044 |
| | | | 600/425 |
| 2014/0126696 A1* | 5/2014 | Xu | G01T 1/295 |
| | | | 378/62 |

* cited by examiner

DETERMINATION OF AN X-RAY IMAGE DATA RECORD OF A MOVING TARGET LOCATION

CROSS-REFERENCE TO RELATED APPLICATIONS

This application claims the benefit of DE 10 2015 205 270.2, filed on Mar. 24, 2015, which is hereby incorporated by reference in its entirety.

TECHNICAL FIELD

Embodiments relate to a method for determining an x-ray image data record of a target location of a patient subjected to a movement using an x-ray device. A number of basic images of the target location are recorded using a basic exposure time in each case, and the x-ray image data record corresponding to an x-ray image recorded with a longer exposure time is determined by combining basic images registered with one another. Embodiments also relate to an x-ray device.

BACKGROUND

The use of x-ray imaging in medical examination and treatment procedures has already been common practice for a long time. If a target location of a patient is to be recorded, two effects may be weighed. On the one hand, with the use of a larger dose, in other words a greater number of x-ray quanta, an improved image quality is achieved because the quanta noise reduces. On the other hand, the radiation dose of the patient with ionizing radiation is also to be kept low.

Obtaining diagnostically usable x-ray images may be problematic if a movement is present in the target location, for instance as a result of the heartbeat or breathing. There is then the additional problem that the desired x-ray dose cannot be applied sufficiently quickly since the x-ray emitters used (x-ray tubes) only allow for a limited dose yield. In order to obtain longer exposure times with reduced motion artifacts, a number of basic images (component images) with a short exposure time may be recorded and registered against one another. Rigid or flexible transformations may be used and are then combined, for example by way of averaging. However, the problem occurs that the object movement in the medical region is very volatile, such that features in the target location sometimes move extremely slowly and sometimes extremely quickly so that it is not possible to define an optimally short basic exposure time for the basic images. If the basic exposure time is too short, the basic images are noisy and may thus be poorly registered. If the basic exposure time is too long, a blurring already occurs in many basic images.

SUMMARY AND DESCRIPTION

The scope of the present invention is defined solely by the appended claims and is not affected to any degree by the statements within this summary. The present embodiments may obviate one or more of the drawbacks or limitations in the related art.

The object underlying the embodiments is to specify a recording method with a moving target location, from which higher quality x-ray image data records having fewer motion artifacts, that correspond to x-ray images with longer exposure times, may be obtained.

To achieve this object, provision is made according to the embodiments with a method of the type cited in the introduction that for each basic image (component image), at least one quality value assigned hereto and relating to the movement in the target location during the recording is determined, and the contribution of a basic image (component image) to the x-ray image data record is determined as a function of the quality value.

Embodiments use the method of "lucky imaging" known from astronomy for medical x-ray images. Embodiments include sorting out the basic images that do not correspond to a certain quality requirement, and giving the images a lower weighting or correcting the images for the final combination, for example for the final averaging. The quality requirement may be checked, for example, by a corresponding assessment criterion. While "lucky imaging" involves atmospheric effects, the procedure may also be applied to an object movement, thus a movement in the target location, so that those basic images may be identified, that are sufficiently sharp. In other words, the images may be identified that have no or few motion artifacts. If the movement in the target location was minimal during the recording of a basic image, this may be suited to determining the x-ray image data record, but if there is a very high speed of movement in the target location, for instance a speed that is faster than an average speed, unacceptable motion artifacts may occur in the basic image, so that the image is not taken into account or is not taken into account in this form. The quality value that is determined in the method describes the movement during the recording duration, for example, a basic exposure time (or image exposure time), for the corresponding basic image. An evaluation of the image may take place in respect of the image's contribution to the x-ray image data record. The contribution may include an exclusion from basic images.

This enables the method of registered averaging from several basic images also then to be applied if the motion speeds change frequently in the target location. An acceptable basic exposure time may then be found without the end result, in other words the x-ray image data record, may be dominated by the quickest movement and thus the final image quality suffering.

In an embodiment, an exclusion criterion evaluating the quality values is used. The basic images assigned to quality values fulfilling the exclusion criterion are not taken into account in the combination or only after a correction process. Basic images that have significant distortion due to movement in the target location, for instance having strong motion artifacts, may be excluded entirely from the combination, in other words from the x-ray image data record, if the images cannot be corrected with correspondingly little effort. The exclusion criterion, or one of the exclusion criteria in the case of several exclusion criteria, may also allow an assessment of the basic image on the basis of the quality value that specifies whether or not a correction is possible. In an embodiment, the basic images are handled according to the quality value as basic images to be taken into account immediately, basic images to be taken into account after a correction process and basic images to be rejected entirely.

In an embodiment, the corresponding basic image may be subjected to a deblurring algorithm as a correction process. Deblurring algorithms are already known in the prior art and allow motion blurriness present in basic images to be eliminated at least partially. A basic image thus corrected, if applicable after a further evaluation, may be supplied again to the combination process, for example, to the averaging process. One embodiment provides that a point spread function is determined for the movement from the movement and/or a movement data describing a comparable movement. The corrected basic image is determined by regularized, inverse filtering with the point spread function. If a point spread function (PSF) may be determined or at least estimated for the movement where the basic image data may be used itself, there is the possibility to remove the motion effects at least partially again by regularized inverse filtering. A procedure of this type is then possible if point spread functions and/or line spread functions are determined and observed in the basic images in order to determine the quality value.

In one embodiment, at least one criterion parameter of the exclusion criterion, for example, a threshold value, is selected on the basis of a user-side requirement. A user may interactively influence which basic images are used to determine the x-ray image data record from the basic images. With a change in the criterion parameter with already existing basic images, the x-ray image data record may be determined again from the basic images. The corresponding x-ray image data record is then, if necessary also in a comparison representation with a previously determined x-ray image data record, displayed to the user, so that the user may assess interactively and in real time how the quality changes. For instance, within the scope of a post processing, more edge definition may be defined while accepting lower numbers of averaged basic images. If the basic images were recorded with a low x-ray dose, a user may also decide to accept motion blurriness in favor of lower noise effects.

In addition or alternatively to using an exclusion criterion, an embodiment may include basic images to be used within the scope of the combination to be included weighted as a function of the quality value. If a weighting is used instead of an exclusion criterion, the quality value describing the motion blurriness may not be used for sorting, but instead used for weighting the basic images within the scope of the combination, for example, averaging. A weighted averaging may take place, for example, that also allows a small contribution to the combination to be obtained from blurred basic images. A weighting of this type may however naturally also then be meaningful if basic images have previously been sorted. Certain basic images may not be included in the combination at all, or only after a correction. An up-to-date quality value relating to a corrected basic image may be determined. The quality value may be based for instance on an effectiveness value of the correction as frequently outputted by deblurring algorithms. When the quality value is determined from the image data of the basic images, the quality value may also be determined completely afresh from the corresponding corrected basic image.

To determine a quality value, different approaches may be used in combination with the use of several quality values. An embodiment provides that a motion speed measured and/or determined from at least one part of the basic images is determined as a quality value in the target location while recording the assigned basic image and/or at least one sharpness parameter is determined describing the sharpness of the picture of a feature of the target location used for registration purposes, for example by evaluating the assigned basic image.

In an embodiment, the determination of the quality value may relate to features that are also used within the scope of the registration of basic images. A registration algorithm may require easily visible markers and/or clearly detectable objects, for example, identifiable features that leave room for as little doubt as possible, for instance edges and/or punctiform features. On the basis of the structurally relatively simple features, the quality value to be used for the suitability for combination may be determined. The sharpness value may be determined as a parameter of a line spread function (LSF). The line spread function of an edge may thus be considered to be a feature. If this indicates a significant blurriness by way of a corresponding sharpness parameter, a high motion speed is assumed in the target location. A similar procedure may also be applied with punctiform features, which may be used as markers during the registration. The point spread function (PSF) may also be used. If the punctiform feature is shown rather "washed out", this indicates high motion activity in the target location. The quality value may be determined from the basic images. The known point and/or line spread functions that relate to the mapping properties of the recording arrangement of the x-ray device, may be taken into account.

An embodiment provides that in order to derive a motion speed from the basic images for a mapping of a feature of the target location used for registration purposes, a spread function is determined and compared with a known reference spread function of the x-ray device. The basic mapping properties of the x-ray device may be known so that additional blurriness of substantially punctiform or linear features originate from the movement in the target location. Point and/or line spread functions may be determined for features that describe the motion blurring originating from the movement. Thus the point and/or line spread functions may also represent a measure of the motion speed in the target location when recording the basic image. An absolute motion speed need not necessarily be specified as the quality value describing the motion speed. Relative motion speeds may also be used. Absolute values for the motion speed may be compared with motion speeds in the target location known from prior knowledge.

The motion speed may also be obtained, in addition or alternatively, from a measurement with a measuring device. An EKG measuring device may measure the heart cycle of the patient. Respiratory belts and suchlike may be used in order to track the cyclical movement of the breathing movement. Other measuring devices may be used, for instance measuring devices for optically scanning the patient, acoustic measuring devices and suchlike. Determining quality values may dispense with additional measuring devices and use the basic image data directly.

In an embodiment, an exclusion criterion evaluating the motion speed is a threshold criterion. The threshold value of motion speed to be exceeded for exclusion purposes is selected as an average motion speed determined from prior knowledge and/or measured on the current patient. An embodiment may include where all images, in which the motion speed was higher than the average motion speed, are not used in the combination or are corrected, while all basic images, the motion speed of which lies below the average motion speed, are used for combination purposes.

Prior knowledge, for instance examinations known in the literature, or prior measurements on the patient, that specify an average motion speed to be expected in the target location, may also be used to determine an expedient basic exposure time. The same basic exposure time may be defined for all basic images as a function of an average motion speed in the target location determined from prior knowledge and/or measured on the current patient. The optimal basic exposure time is in this way configured on the average speed to be expected in the target location. For instance for the coronary vessel as a target location the average motion speed lies in the range of 23 to 25 mm per second. For average motion speeds of this type, basic exposure times may be applied for instance in the range of 7 to 9 milliseconds, as are already used in cardiology. If the average motion speed is higher, shorter basic exposure times may be applied, if the average motion speed is lower, this allows for the use of a longer basic exposure time. Other previously known motion parameters of the movement in the target location may be used if a basic exposure time to be used is to be estimated. For example, basic exposure times may be geared to the average duration of relative rest phases.

Current measured values of an EKG measuring device may also be used within the scope of determining the quality value. The current measured values are used to trigger the recording of the basic images in the motionless phases of the movement. With cyclical movements in the target location, the course of which may be estimated from the outset, there is the possibility of intentionally selecting movement phases, in which the target location is rather motionless. The number of basic images, that have significantly blurred movements, may thus be reduced. Alternatively if there is no information relating to the current movement in the target location available basic images may be recorded immediately one after the other as a cohesive image series.

Aside from the method an embodiment also relates to an x-ray device having a control device embodied to perform the method. All embodiments relating to the method may be analogously transferred to the x-ray device, so that the advantages already cited may also be achieved herewith.

BRIEF DESCRIPTION OF THE DRAWINGS

Further advantages and details of the present invention will become apparent from the embodiments described below as well as with reference to the drawing.

DETAILED DESCRIPTION

Figure 1:
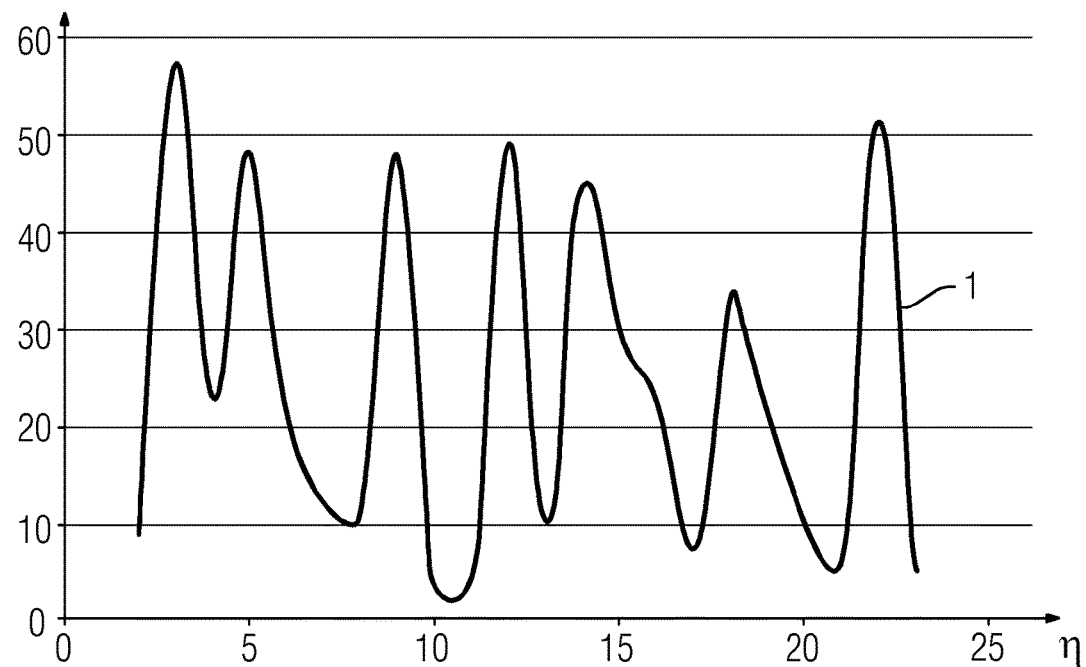
FIG. 1 depicts an example speed curve of a point in a target location to be recorded.

FIG. 1 depicts, by way of example for one point in the coronary vessels, the speed v in the object plane in millimeters per second plotted against the time, currently mapped by the image number n during a continuous, consecutive recording of basic images of the target location containing the coronary vessels and during the use of a fixed basic exposure time. The curve 1 identifies that strong fluctuations in the motion speed occur about the average value of here 24 mm/s, as known from prior knowledge. Consequently, some of the basic images recorded here with a basic exposure time of 8 milliseconds indicate significant blurriness and/or other motion artifacts.

Figure 2:
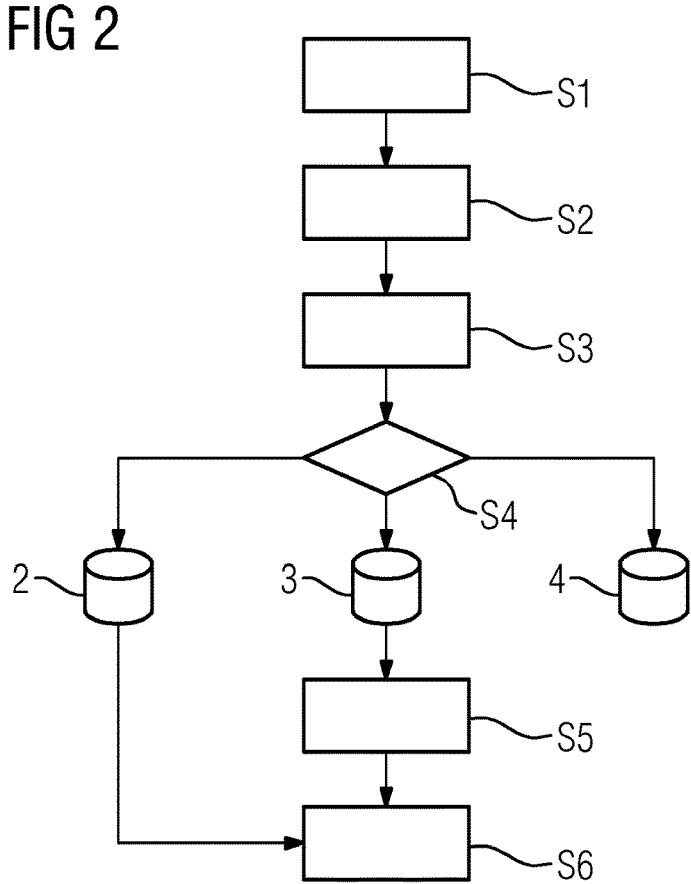
FIG. 2 depicts a flow diagram according to an embodiment.

In order to be able to combine a high quality x-ray image data record from the basic images by way of averaging, a method, depicted in FIG. 2, uses a quality value describing the motion speed in order to sort the basic images according to basic images to be taken into account immediately, basic images to be corrected and basic images to be completely rejected.

A suitable basic exposure time (image exposure time) is firstly selected in act S1. The selection takes place by taking the prior knowledge relating to the target location into account, such that the average motion speed is at approx. 24 mm/s at significantly moving edges, for example, the coronary vessels. An assigned basic exposure time for the individual basic images of 8 milliseconds is defined as a function thereof. Smaller average motion speeds result in longer basic exposure times. Greater average motion speeds result in shorter basic exposure times.

In act S2, a predetermined number of basic images (component images) is recorded with the basic exposure time, for instance 20 to 30 basic images. The x-ray device is used. The control device of the x-ray device actuates the recording arrangement of the x-ray device in order to be able to record basic images. In certain embodiments an EKG measuring device may be used while recording the basic images in a triggered manner such that the basic images are measured in motionless phases of the target location.

In act S3, a quality value is determined for each basic image, for example, on the basis of the image data of the basic image itself. An absolute motion speed for features of the target location, that are mapped therein, are currently determined as a quality value. The features may be detected and are to be used subsequently also to register basic images with one another. For example, this involves features that are mapped as edges or substantially in a punctiform manner. With regard to the features, point spread functions or line spread functions are determined depending on their nature. The point spread functions or line spread functions may be compared with reference point spread functions or reference line spread functions describing the mapping properties of the x-ray device. The point spread functions or line spread functions may be used to extract the blurriness effects that originate from the movement of the target location. On the basis of this blurriness caused by the movement, such as is mapped by the spread functions, a value for the motion speed of the corresponding feature may be determined as a quality value. Sharpness parameters may be derived from the spread functions or otherwise, that describe the movement of the feature and may be used as a quality value. A further possibility to determine quality values naturally is to measure with a measuring device in parallel with the recording of the respective basic image. The use of additional measuring devices may be avoided in certain embodiments.

In act S4, at least one selection criterion that evaluates the at least one quality value, is evaluated for each basic image. The basic images may be divided into three groups 2, 3, 4 by the selection criterion. Basic images, the motion speed of which is lower than the average motion speed already mentioned, may be sorted into a first group 2 that contains basic images to be taken into account immediately. If the motion speed lies between the cited first threshold value and a second threshold value describing a higher motion speed, when the basic image is recorded, the corresponding basic images are sorted into a second group 3 including basic images to be corrected. If the motion speed for a basic image is above the second threshold value, the basic image is sorted into the third group 4 of basic images that are to be excluded entirely.

If the basic images of group 4 are rejected entirely and not taken into account further, a correction process is performed in act S5 for the basic images of group 3. The correction process include applying a blurring algorithm. The point spread function determined in act S3 that describes the effects of the movement is used to determine a corrected basic image by regularized, inverse filtering with the point spread function. The corrected basic image is further suited to consideration when determining the x-ray image data record. For corrected basic images, a new quality value similar to act S3 is determined from the image data. In other embodiments, provision may also be made to modify the quality value, for example, the motion speed, in a fixed and/or dynamic manner on the basis of the effect of the correction.

In act S6, the x-ray image data record is then determined from the basic images of group 2 and the corrected basic images of group 3 by weighted averaging. The basic images corrected where applicable were registered overall with one another. For registration purposes, the easily identifiable features already discussed are used. The weighting of the individual basic images of group 2 to be used immediately and corrected basic images of group 3 is determined according to the quality value; basic images less influenced by movement in the target location are weighted more significantly than basic images influenced more significantly by the movement in the target location.

An x-ray image data record is obtained that has less diminished quality due to movement effects and corresponds to an x-ray image with a longer exposure time than the basic exposure time.

In an embodiment, the exclusion criteria of act S4 may be skipped. In an embodiment, a weighted combination of the basic images is performed and a sorting may show better results.

Figure 3:
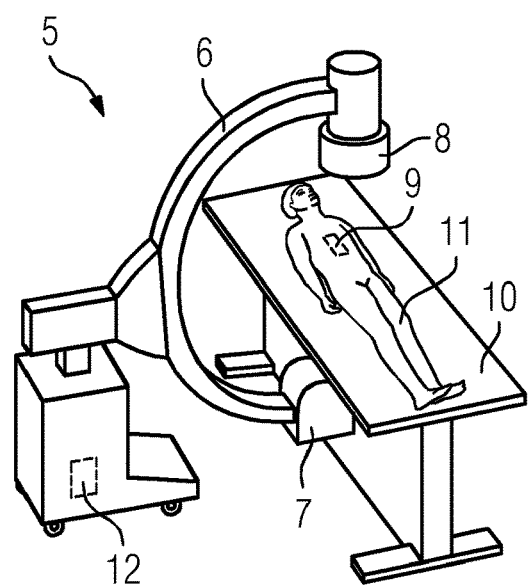
FIG. 3 depicts an example x-ray device.

FIG. 3 depicts a block diagram of an x-ray device 5 that includes a C-arm 6, on which an x-ray emitter 7 and an x-ray detector 8 are arranged opposite one another. The recording arrangement is already aligned here such that a target location 9 of a patient 11 positioned on a patient couch 10 may be recorded. The target location 9 is subjected to a movement, for example, a movement triggered by the heartbeat.

The x-ray device 5 further includes a control device 12, which is configured to perform the method. After choosing a basic exposure time the basic images may be recorded. Moreover, the control device 12 may have a quality value determination unit for performing act S3, a sorting unit for performing act S4, a correction unit for performing act S5 and a combination unit for performing the act S6.

Although the invention has been illustrated and described in greater detail with reference to an embodiment, the invention is not limited by the examples disclosed and other variations may be derived herefrom by the person skilled in the art without departing from the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining an x-ray image data record of a target location of a patient subjected to a movement using an x-ray device, the method comprising:
   recording a plurality of component images of the target location using an image exposure time;
   registering the plurality of component images with one another;
   determining one or more quality values related to the movement of the target for each component image of the plurality of component images, the one or more quality values including at least a motion speed calculated as a comparison between a spread function of at least two or more of the plurality of component images and a reference spread function of the x-ray device;
   selecting as a function of the one or more quality values a contribution of one or more basic images of the plurality of component images; and
   combining the one or more component images into the x-ray image data record as a function of the selected contribution of the one or more component images.

2. The method as claimed in claim 1, wherein the one or more quality values further includes an exclusion criterion, wherein basic images fulfilling the exclusion criterion are not selected until undergoing a correction process.

3. The method as claimed in claim 2, wherein the correction process includes a deblurring algorithm.

4. The method as claimed in claim 2, further comprising:
   determining a point spread function for the movement from the movement or movement data describing a comparable movement, wherein the correction process includes is regularized, inverse filtering with the point spread function.

5. The method as claimed in claim 2, wherein at least one criterion parameter of the exclusion criterion is selected on the basis of a user requirement.

6. The method as claimed in claim 5, further comprising:
   generating an updated x-ray image data record using a different criterion parameter.

7. The method as claimed in claim 1, wherein combining the x-ray image data record comprises:
   combining the one or more component images to be used;
   wherein the component images are weighted as a function of the contribution.

8. The method as claimed in claim 1, wherein determining one or more quality values further comprises:
   determining at least one sharpness parameter describing a sharpness of the mapping of a feature of the target location.

9. The method as claimed in claim 8, wherein the sharpness value is determined as a parameter of a line spread function.

10. The method as claimed in claim 1, wherein the image exposure time is defined as a function of the movement.

11. The method as claimed in claim 1, further comprising:
    triggering the recording of the component images by using an EKG measuring device.

* * * * *